United States Patent
Heese et al.

(10) Patent No.: US 10,485,992 B2
(45) Date of Patent: Nov. 26, 2019

(54) ULTRASOUND GUIDED RADIOTHERAPY SYSTEM

(71) Applicant: KONINKLIJKE PHILIPS N.V., Eindhoven (NL)

(72) Inventors: Harald Sepp Heese, Hamburg (DE); Torbjorn Vik, Hamburg (DE); Heinrich Schulz, Hamburg (DE); Christian Buerger, Hamburg (DE); Jochen Peters, Norderstedt (DE)

(73) Assignee: Koninklijke Philips N.V.

( * ) Notice: Subject to any disclaimer, the term of this patent is extended or adjusted under 35 U.S.C. 154(b) by 162 days.

(21) Appl. No.: 15/575,826

(22) PCT Filed: Jun. 6, 2016

(86) PCT No.: PCT/EP2016/062769
§ 371 (c)(1),
(2) Date: Nov. 21, 2017

(87) PCT Pub. No.: WO2016/202620
PCT Pub. Date: Dec. 22, 2016

(65) Prior Publication Data
US 2018/0147419 A1 May 31, 2018

(30) Foreign Application Priority Data
Jun. 19, 2015 (EP) .................................... 15172852

(51) Int. Cl.
*A61N 5/10* (2006.01)
*A61B 90/00* (2016.01)

(52) U.S. Cl.
CPC ........... *A61N 5/1049* (2013.01); *A61N 5/107* (2013.01); *A61B 2090/378* (2016.02); *A61N 2005/1058* (2013.01)

(58) Field of Classification Search
None
See application file for complete search history.

(56) References Cited

U.S. PATENT DOCUMENTS

| 5,997,479 A | 12/1999 | Savord et al. |
| 6,013,032 A | 1/2000 | Savord |
| (Continued) | | |

FOREIGN PATENT DOCUMENTS

JP 2006158678 A 6/2006

OTHER PUBLICATIONS

Ecabert, O. et al "Automatic Model-Based Segmentation of the Heart in CT Images", IEEE Transactions on Medical Imaging, vol. 27, No. 9, pp. 1189-1201.

(Continued)

*Primary Examiner* — Hoon K Song

(57) ABSTRACT

It is an object of the invention to provide for a system, method and computer program product enabling monitoring of effects of intrafraction motion during the radio therapy treatment. According to a first aspect of the invention this object is achieved by an ultrasound guided radiotherapy system, comprising a radiotherapy system configured for providing a radiation treatment by means of a radiation beam to a treatment target. The ultrasound guided radiotherapy system further comprises an ultrasound imaging system configured for acquiring a 3D online image of the treatment target and/or an organ at risk during the radiation treatment. It further comprises detection means configured for detection, in the 3D online image, parts representing the treatment target and/or organ at risk and selection means configured for selecting a view plane through the treatment target and/or an organ at risk represented by the detected parts in the 3D online image and a display configured to display a 2D image of part of the treatment target and/or organ at risk along the view plane, wherein the display is (Continued)

further configured to display a treatment margin and/or an outline of an actual radiation beam in relation to the treatment target and/or organ at risk.

15 Claims, 5 Drawing Sheets

(56) References Cited

U.S. PATENT DOCUMENTS

| | | |
|---|---|---|
| 6,283,919 B1 | 9/2001 | Roundhll et al. |
| 6,443,896 B1 | 9/2002 | Detmer |
| 6,458,083 B1 | 10/2002 | Jago et al. |
| 6,530,885 B1 | 3/2003 | Entrekin et al. |
| 6,623,432 B2 | 9/2003 | Powers et al. |
| 6,961,405 B2 | 11/2005 | Scherch |
| 8,189,738 B2 | 5/2012 | Dussault et al. |
| 9,561,016 B2 | 2/2017 | Pagoulatos et al. |
| 2006/0113482 A1 | 6/2006 | Pelizzari et al. |
| 2010/0222676 A1 | 9/2010 | Ogihara et al. |
| 2011/0075807 A1 | 3/2011 | Liu et al. |
| 2012/0157842 A1 | 6/2012 | Davis et al. |
| 2014/0107390 A1 | 4/2014 | Brown et al. |
| 2014/0275707 A1 | 9/2014 | Lidstrom et al. |
| 2015/0314138 A1* | 11/2015 | Maurer ............... A61B 6/5247 600/411 |
| 2019/0117998 A1* | 4/2019 | Han ..................... G06T 7/246 |

OTHER PUBLICATIONS

Su, Y. et al., "Marker-less Intra-Fraction Organ Motion Tracking—A Hybrid ASM Approach". IEEE International Workshop on Imaging Systems and Techniques—IST 2007, Krakow, Poland, May 4-5, 2007.

* cited by examiner

ULTRASOUND GUIDED RADIOTHERAPY SYSTEM

CROSS-REFERENCE TO PRIOR APPLICATIONS

This application is the U.S. National Phase application under 35 U.S.C. § 371 of International Application Serial No. PCT/EP2016/062769, filed on Jun. 6, 2016, which claims the benefit of European Patent Application No. 15172852.4, filed on Jun. 19, 2015. This application is hereby incorporated by reference herein.

FIELD OF THE INVENTION

The invention relates to a system and device in the field of ultrasound guided radiotherapy. The invention further relates to a method and a computer program product in the field of ultrasound guided radiotherapy.

BACKGROUND OF THE INVENTION

In external radiotherapy, the patient is treated with high-energy radiation e.g. generated by a linear accelerator ('linac'). The linac could for example be mounted on a rotating gantry, but it could also be mounted to a robotic radiosurgery system. External radiotherapy is generally delivered by means of a plurality of daily treatment fractions. Radiation can be continuously delivered during a single fraction while rotating the gantry, which is called "volumetric modulated arc therapy" (VMAT) or only be delivered while the gantry is not moving and shut off while rotating the gantry (step-and-shoot treatment). For VMAT, the treatment time is typically in the range of 2-4 minutes per fraction while for step-and-shoot it is typically in the range of 5-15 minutes per fraction. For a good treatment outcome a balance should be found between giving enough radiation dose to the treatment target, while sufficiently sparing neighbouring organs at risk. Providing a too high radiation dose to an organ at risk is likely to result in unwanted side-effects.

A treatment plan, describing beam directions, shapes and intensities, depends on a patient's anatomy and on a treatment target (tumor type, tumor location, size, infiltration, etc.). For this purpose a volumetric image of the patient is acquired before treatment. This image is called a treatment planning image. For acquisition of the treatment planning image, the patient is positioned in the same way as on the treatment table. The planning image, generally a CT image, represents a 'snapshot' of the patient anatomy at a time point prior to treatment. In some cases, further images are acquired in order to improve the target delineation (MR or PET).

The treatment plan which is based on the snapshot of the patient anatomy cannot account for anatomical changes within the patient, e.g. due to internal organ motion. Such changes are generally grouped into inter-fraction and intra-fraction changes. Examples of inter-fraction changes are weight-loss and tumour shrinkage/growth. Examples of intra-fraction changes are breathing, bladder filling, muscular relaxation, couching, and others. To monitor intra-fraction motion, online images could be used, wherein "online" refers to imaging during the actual radiotherapy fraction. To deal with anatomical changes occurring after the planning image, the target definition is generally extended by a treatment margin. The resulting volume of the treatment target and this treatment margin is called planning target volume (PTV).

US 2011/0075807 A1 describes an adaptive imaging method of monitoring intrafraction target motion during radiotherapy. This method includes using simultaneous Mega-Voltage (MV) and Kilo-Voltage (KV) imaging to determine an initial 3D target position. 2D target position is monitored using MV imaging during radiotherapy delivery and is in combination with an online-updated characterization of target motion that are disposed to estimate if the target has moved beyond a 3D threshold distance.

SUMMARY OF THE INVENTION

It is an object of the invention to provide for a system, method and computer program product enabling monitoring of effects of intrafraction motion during the radiotherapy. According to a first aspect of the invention this object is achieved by an ultrasound guided radiotherapy system, comprising a radiotherapy system configured for providing a radiation treatment by means of a radiation beam to a treatment target and an ultrasound imaging system configured for acquiring a 3D online image of the treatment target and/or an organ at risk during the radiation treatment and detection means configured for detection, in the 3D online image, parts representing the treatment target and/or organ at risk;

selection means configured for selecting a view plane through the treatment target and/or an organ at risk represented by the detected parts in the 3D online image;

a display configured to display a 2D image of part of the treatment target and/or organ at risk along the view plane, wherein the display is further configured to display a treatment margin and/or an outline of an actual radiation beam in relation to the treatment target and/or organ at risk.

During a second aspect of the invention this object is achieved by a method according to claim 14 and a computer program product according to claim 15. This object is also achieved by selection means according to claim 13.

It is an insight of the inventors that one of the main difficulties when dealing with intra-fraction motion is that comprehensive 3D assessment of volumetric, real-time patient anatomy is not feasible for a clinical operator. Furthermore, automatic methods for anatomy tracking can fail, giving rise to the need for fail-safe fall-back methods.

With the system and method according to the invention an automatic selection is made of a 2D view plane geometry through the treatment target and/or organ at risk and by displaying an image along the view plane in combination with a treatment margin and/or an outline of the actual radiation beam. So a clinical operator on the one hand has a practical, easy-to-use surveillance available, while he/she on the other hand can be confident that no significant changes of the PTV are being missed.

Therefore, by means of the invention important information about treatment target and/or organ at risk can be retrieved without the need of a comprehensive 3D assessment of the patient's anatomy. The system could be configured such that the view plane is regularly synchronized with the direction of the radiation beam. These measures may enable an operator to better determine it the patient is treated as planned. If the position of the treatment target and/or organ at risk is not within a predetermined limit or treatment margin, measures could be taken e.g. the radiotherapy could be (temporarily) stopped, and the patient could be repositioned to align with the treatment margins again.

According to an embodiment of the invention, the selection means are configured to select the view plane based on an actual direction of the actual radiation beam. This is advantageous, because the actual direction of the actual radiation beam determines what changes in the position and/or orientation of the treatment target and/or organ at risk may have a strong effect on the delivered dose. The view plane could be selected such that those relevant changes are likely to be captured. One possible option is to select the view plane such that an actual direction of an actual radiation beam is substantial perpendicular to the view plane. Treatment target movement along the radiation beam direction likely causes less deviations from the treatment plan than movement perpendicular to this direction, because sharp gradients in dose are likely to occur in the direction perpendicular to the radiation beam and not in the direction along the radiation beam.

The above embodiment would determine the orientation of the view plane. According to an embodiment of the invention, the position of the view plane would be selected such that in the 2D slice along the view plane an outline of the treatment margin best matches according to a predetermined criterion a cross-sectional outline of the radiation beam. Movement of the treatment target at these positions may likely result in a deviation between the planned and delivered dose to the treatment target and/or organ at risk. Therefore it is advantageous to monitor the treatment target and/or organ at risk at this position. This predetermined criterion could for example be a Dice coefficient, but it could also be the presence of a 3D extremity point. The 3D extremity point is a point of the treatment target volume. In case all target points are enclosed by the treatment margin or the actual outline of the radiation beam, the 3D extrimity point the point of the treatment target that if inside a volume enclosed by the treatment margin or the actual outline of the radiation beam is the one point being closest to the treatment margin or beam outline. In case some target points are exceeding the treatment margin or beam outline, the 3D extrimity point is the one point being furthest away from that treatment margin. Positioning the view plane such that it covers the 3D extremity point is advantageous, since movement of the extremity point may cause large deviations between a planned dose to the treatment target and a delivered dose to the treatment target. This in turn may affect treatment outcome.

According to an embodiment of the invention, the selection means is configured to select the view plane based on information about the treatment target and/or organ at risk. For example parts of the treatment target may be of special interest because the tumor aggressiveness is higher at this location and therefore dose coverage is of higher importance. Also, some parts of the organ at risk may be more critical than others. According to one embodiment of the invention the selection means is configured such that the view plane is selected such that it contains a main vector of motion of the treatment target and/or organ at risk. Motion in some direction is more likely to occur than in other directions. For example the position of certain treatment targets and/or organs at risk is largerly affected by breathing or bowel movement. It is advantageous to position the view plane such that this main motion is contained in the view plane, because this movement may affect the delivered dose to the treatment target and/or organ at risk.

Also 3D extremity point may be of special interest and the view plane may be selected such that it contains the 3D extremity point. It is especially advantageous to only consider the part of the treatment target that is in the actual outline of the radiation beam to determine the 3D extremity point, as movement of other parts of the treatment target are of less relevance.

By selecting the view plane in one of the above mentioned ways, the likelihood that target and/or organ at risk motion get detected that cause large deviations from the treatment plan is increased.

According to another embodiment of the invention the radiotherapy system comprises multiple collimator leaves and the display is configured to display subsequent images and is further configured to display a projection of the multiple collimator leaves and to display the subsequent images such that the orientation of the multiple collimator leaves is the same in the subsequent images. This embodiment is advantageous, because it makes it easier for an operator to evaluate subsequent images and to appreciate the collimator leave travel path.

The ultrasound guided radiotherapy system comprises detection means configured to cause, when executed on the processor, a detection of the treatment target on one or a plurality of images acquired by the medical imaging system. This treatment target detection could be achieved by means of image registration, wherein the online image could be registered to the planning image on which the treatment target has already been segmented. Other methods for image segmentation or detection are known in the art of image analysis and could also be used by the detection means to detect the position and/or orientation and/or delineation of the treatment target and/or organ at risk. One possibility would be a method similar to what is described in Ecabert et al Automatic Model-Based Segmentation of the Heart in CT Images, IEEE TRANSACTIONS ON MEDICAL IMAGING, VOL. 27, NO. 9, pages 1189-1201.

In another embodiment with automatic treatment target detection, and limited time history of the treatment target positions, the image guided radiotherapy system is configured to select the view plane such that two 3D extremity-points from the treatment target surface at two different time points are contained. The image guided radiotherapy system could be configured such that the two time points are selected at the extremities of the main motion vector.

The ultrasound guided radiotherapy system could also be configured to select multiple view planes. This is also advantageous if extremity points occur at multiple positions in the treatment target, which are not covered by a single image acquired along the view plane.

According to another embodiment of the invention, the display is further configured to visualize the orientation of an actual view plane, such that the operator could appreciate the orientation of the view plane. The orientation could for example be shown relative to the 3D online image or relative to a visualization of a human anatomy.

All these embodiments could be implemented in a computer program product, which computer program product comprises executable code to perform method steps of the invention.

These and other aspects of the invention will be apparent from and elucidated with reference to the embodiments described hereinafter.

DETAILED DESCRIPTION OF THE INVENTION

Figure 1:
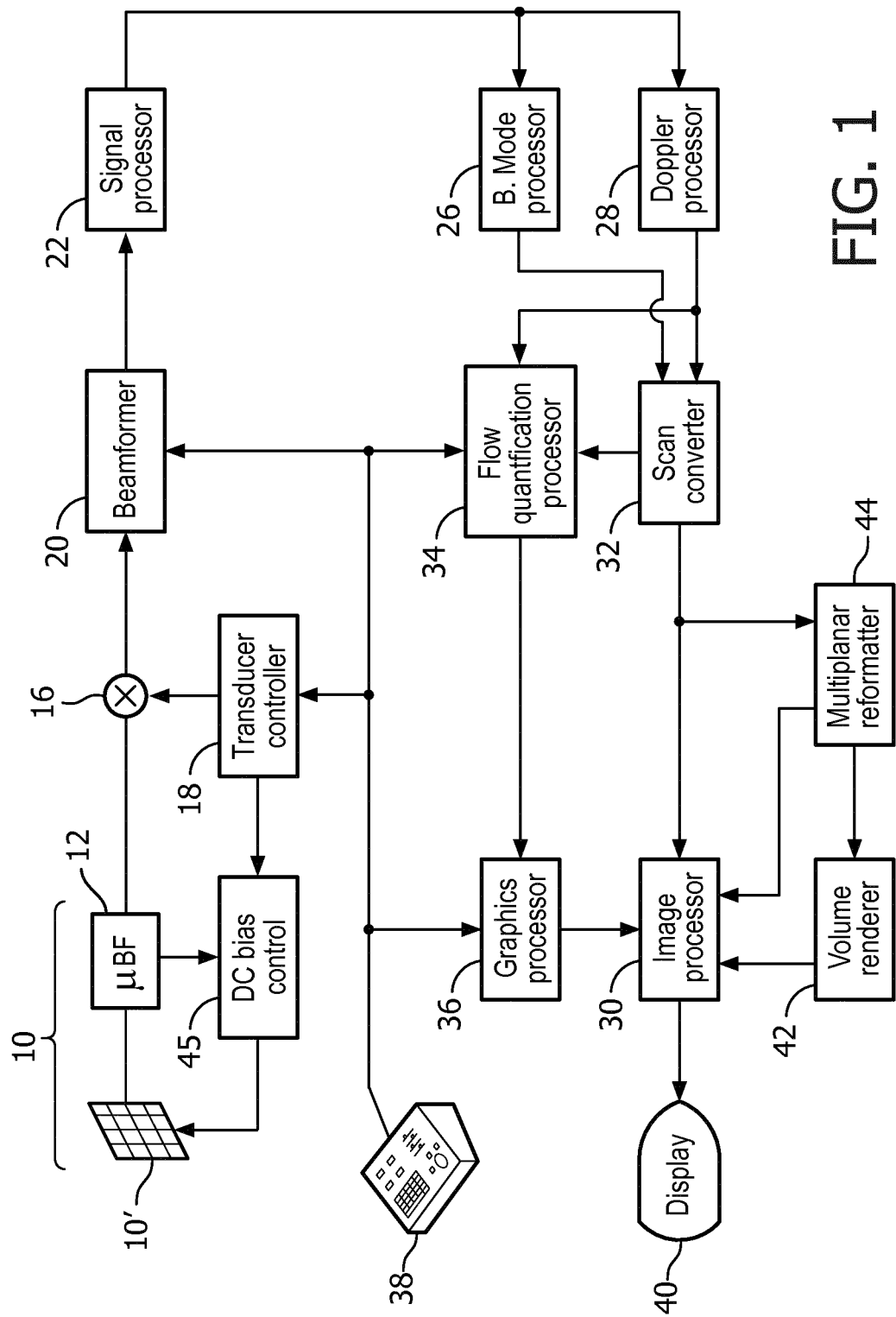
FIG. 1 diagrammatically shows an ultrasound imaging system.

Referring first to FIG. 1, an ultrasonic diagnostic imaging system with an array transducer probe is shown in block diagram form. In FIG. 1 a CMUT transducer array 10' is provided in an ultrasound probe 10 for transmitting ultrasonic waves and receiving echo information. The transducer array 10' may alternatively comprise piezoelectric transducer elements formed of materials such as PZT or PVDF. The transducer array 10' is a one- or a two-dimensional array of transducer elements capable of scanning in a 2D plane or in three dimensions for 3D imaging. The transducer array is coupled to a microbeamformer 12 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception and protects the main beamformer 20 from high energy transmit signals when a microbeamformer is not used and the transducer array is operated directly by the main system beamformer. The transmission of ultrasonic beams from the transducer array 10 under control of the microbeamformer 12 is directed by a transducer controller 18 coupled to the microbeamformer by the T/R switch and the main system beamformer 20, which receives input from the user's operation of the user interface or control panel 38. One of the functions controlled by the transducer controller is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets DC bias voltage(s) that are applied to the CMUT cells.

The partially beamformed signals produced by the microbeamformer 12 on receive are coupled to a main beamformer 20 where partially beamformed signals from individual patches of transducer elements are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducer elements of a transducer array can contribute efficiently to a single beamformed signal.

The beamformed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor may also perform additional signal enhancement such as speckle reduction, signal compounding, and noise elimination. The bandpass filter in the signal processor can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B mode processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.)

The structural and motion signals produced by the B mode and Doppler processors are coupled to a scan converter 32 and a multiplanar reformatter 44. The scan converter arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40.

The quantification processor may receive input from the user control panel 38, such as the point in the anatomy of an image where a measurement is to be made. Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 10' and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

Figure 2:
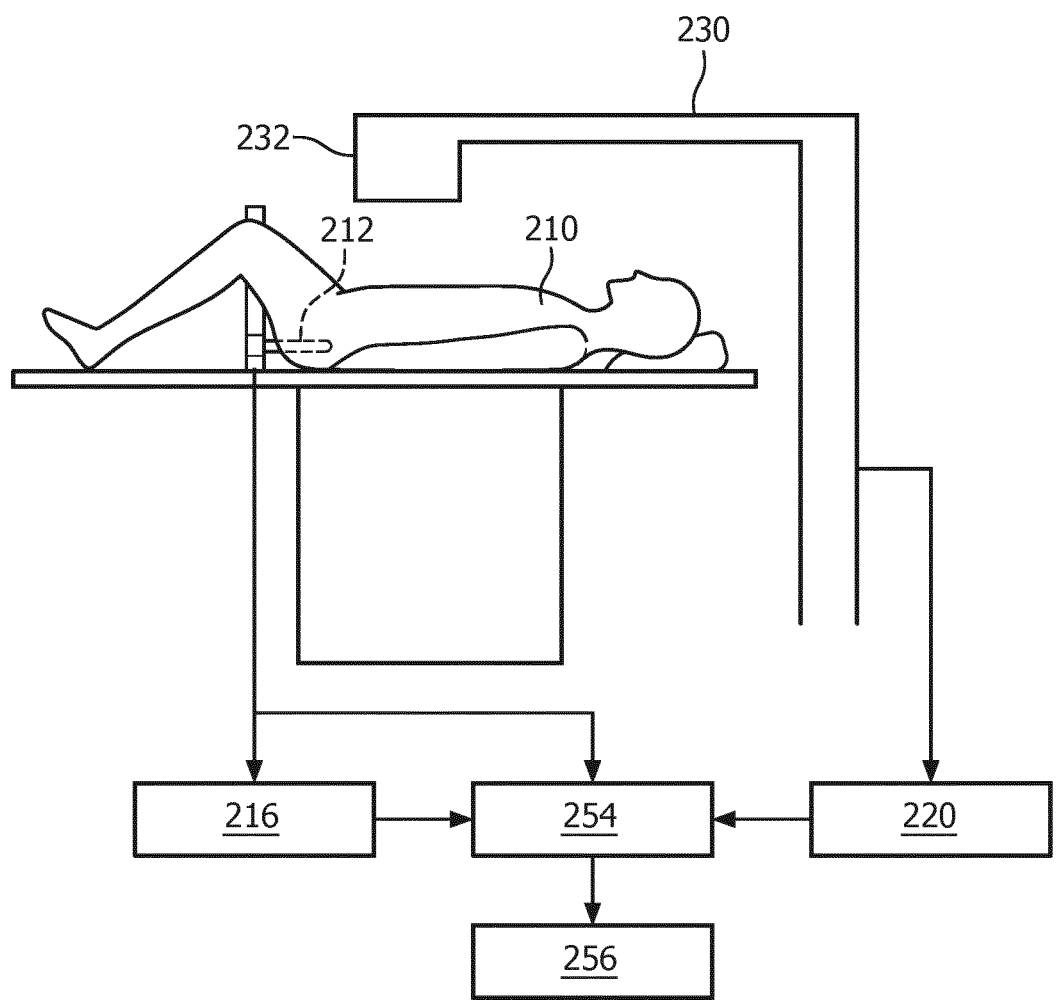
FIG. 2 shows an ultrasound guided radiotherapy system according to the invention and FIG. 3 shows an example of how the view plane can be selected and FIG. 4 shows an illustration of 3D extremity points and FIG. 5 shows another illustration of an 3D extremity point and FIG. 6 diagrammatically shows a method for assisting in validating if an intrafraction motion of a treatment target and/or organ at risk remains within a preset limit during radiotherapy.

FIG. 2 shows an ultrasound guided radiotherapy system according to the invention, comprising an ultrasound imaging system and a radiotherapy system.

Figure 4:
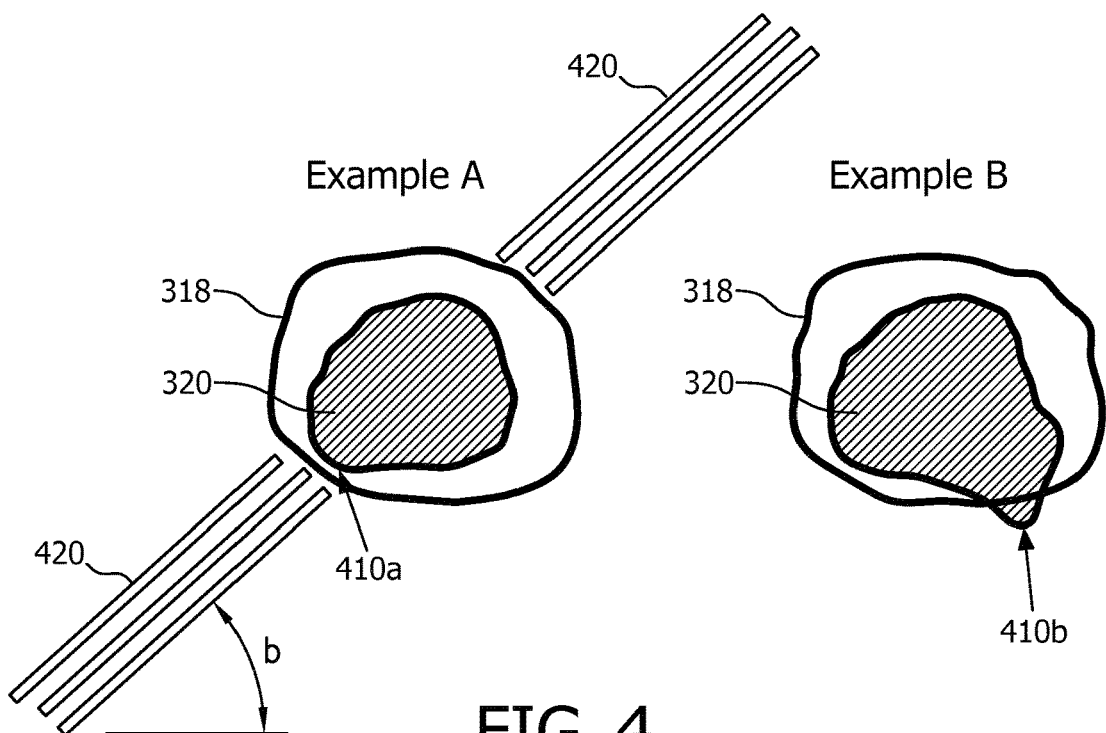

The radiotherapy system 232 includes a housing 230 or other support or body supporting a radiation source arranged to move or revolve around the subject. The radiotherapy system 232 may contain a multi-leaf collimator (MLC) 420 (FIG. 4). The combination of the multi-leaf collimator with the motion of the radiation source around the subject allows the delivery of complex dose distributions by means of for example VMAT or step and shoot intensity modulated radiation therapy. If treatment target motion and/or motion of the organ at risk exceeds a pre-set limit or treatment margin, the radiotherapy could be paused or stopped by the operator. The radiotherapy system is configured to load a treatment plan. Prior to the treatment fraction the patient 210 is aligned with the radiotherapy system, such that his position and orientation match the position and orientation of the planning stage. The ultrasound guided radiotherapy system is configured to deliver radiation beams according to the treatment plan.

The ultrasound system is configured to acquire 3D online images. The trancducer matrix 10" of the ultrasound system is positioned such that its position is fixed relative to the patient. Alternatively, the position of the ultrasound system could be tracked, e.g. by means of the use of optical markers. Also, the ultrasound image could be registered with the planning CT image. In these ways the position of the ultrasound imaging system can be matched with the radiotherapy system.

Detection means 216 are configured for detection of the treatment target and/or organ at risk on the 3D online image acquired by the ultrasound system 212. This detection could for example be achieved by registration of the 3D online image with the planning image, on which the treatment target and organ at risk have been delineated. Detection could also be achieved by means of other detection or segmentation methods, for example by means of atlas based methods, or by a method similar as a method similar to what is described in Ecabert et al Automatic Model-Based Segmentation of the Heart in CT Images, IEEE TRANSACTIONS ON MEDICAL IMAGING, VOL. 27, NO. 9, pages 1189-1201. Furthermore, the operator could be requested to provide a first delineation of the treatment target and/or organ at risk, which is then used by the system to detect the target in subsequent images.

A controller 220 of the radiotherapy system 232 which controls its position and orientation based on the treatment plan and thereby the direction of the treatment beam provides the information of the actual direction of the radiation beam to the selection means 254. A 2D image of the treatment target and/or organ at risk along the view plane is shown to the operator on display 256.

Figure 3:
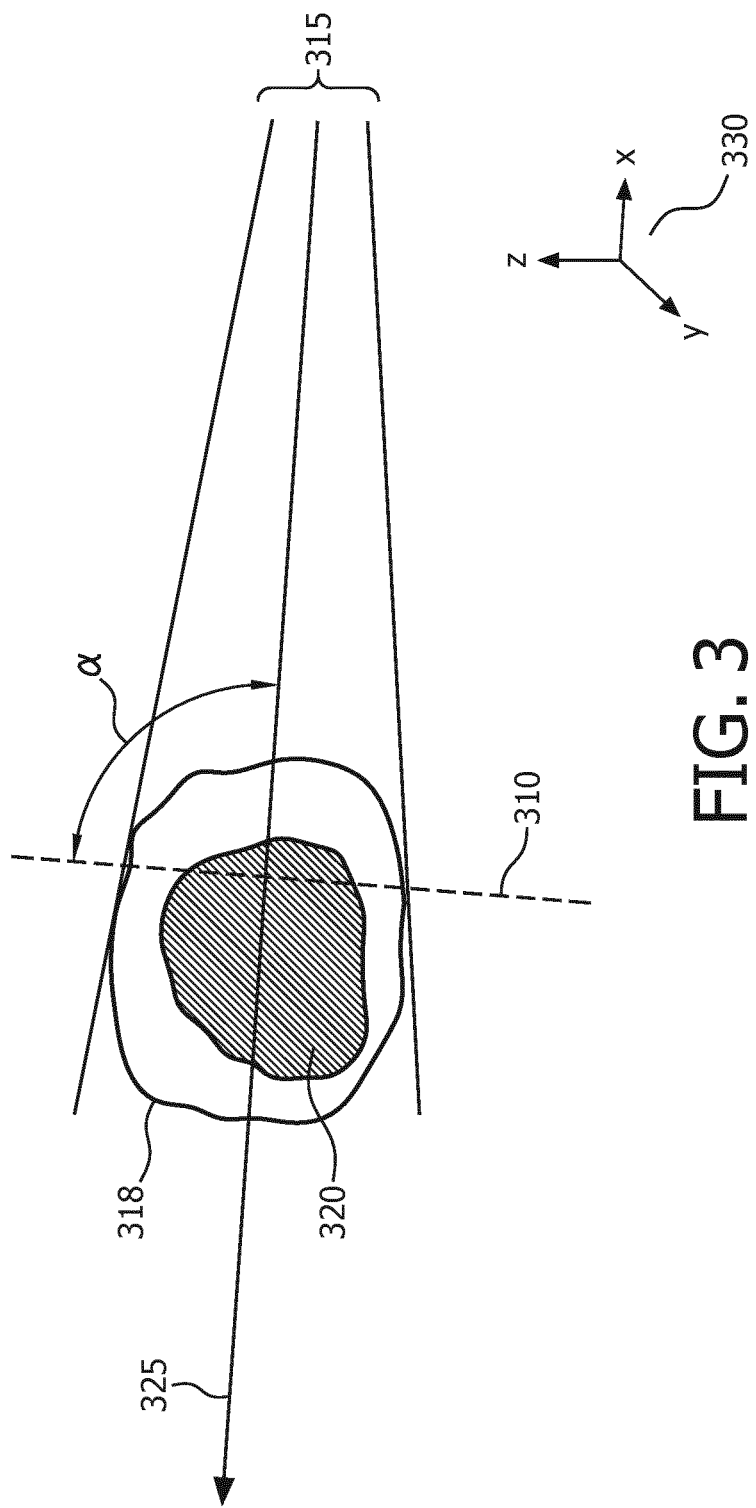

FIG. 3 shows an example of how the view plane can be selected. A radiation beam 315 is delivered by the radiotherapy system 232 to the treatment target 320, such that the treatment target plus a predetermined treatment margin 318 get irradiated. The treatment margin 318 is determined such that it in general would sufficiently compensate for intrafraction motion. A coordinate system 330 could be defined, which rotates with the radiotherapy system. Hereby, the x-axis is parallel to the beam direction 325. The position and orientation of the radiotherapy system 232 determines the direction of the radiation beam 315. The selection means 254 uses the information about the position and orientation of the radiotherapy system 232 to select a view plane 310 substantially perpendicular to the direction 325 of the radiation beam 315. So, angle α between the view plane and the radiation beam is preferably between 80 and 100 degrees and more preferably between 85 and 95 degrees. Hereby, the orientation of the view plane is determined. This orientation is substantially parallel to the YZ-plane. For the x-coordinate of the plane any value could be chosen as long as the resulting view plane contains (part of) the treatment target and/or organ at risk. The ultrasound guided radiotherapy system is then configured to render an image of the treatment target and/or organ at risk from the online 3D image along the view plane, which could be shown to the operator on display 256 of the ultrasound guided radiotherapy system. The display could also be configured to indicate the orientation of the view plane relative to the 3D online image or the patient's anatomy.

According to embodiments of the invention, the x-coordinate is chosen such that the view plane contains the centre of mass of the treatment target. Alternatively, the selection means is configured to select the view plane such that in the 2D slice along the view plane an outline of the treatment margin best matches according to a predetermined criterion a cross-sectional outline of the radiation beam. One possible example of such a predetermined criterion could be the presence of a 3D extremity point. The x-coordinate of the view plane could be determined based on a location of one or more extremity points of the treatment target. FIG. 4 shows an explanation of extremity points. The extremity point 410a or 410b is the point of the treatment target 320 that if inside a volume enclosed by the predetermined treatment margin 318 is closest to the treatment margin 410a or if exceeding the volume enclosed by the predetermined treatment margin 318 is furthest from the treatment margin 410b. In cases where the 3D extremity point is determined by the actual outline of the radiation beam the 3D extremity point may change when the actual direction and/or shape of the actual radiation beam changes. In contrast, if the 3D extremity point is determined based on the treatment margin, it is not affected by the actual direction and/or shape of the actual radiation beam.

FIG. 4 also displays another embodiment of the invention. According to this embodiment the radiotherapy system comprises multiple collimator leaves and the display is configured to display subsequent images and is further configured to display a projection of the multiple collimator leaves 420 and to display the subsequent images such that the orientation of the multiple collimator leaves is the same in the subsequent images. This embodiment is advantageous, because it makes it easier for an operator to evaluate subsequent images. So, in this embodiment an in-plane angle β (FIG. 4), describing a rotation in the YZ-plane (FIG. 3), will be the same for subsequent images.

Figure 5:
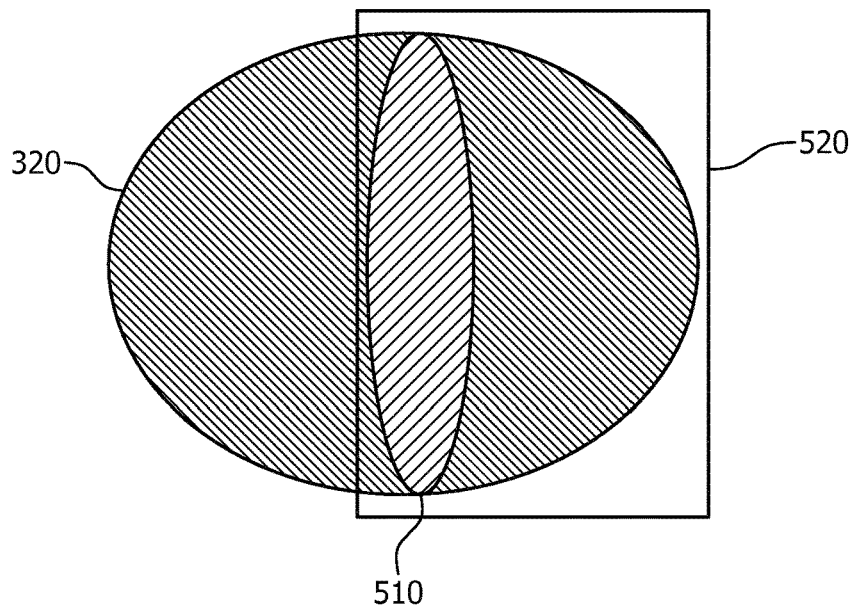

FIG. 5 shows another illustration of an 3D extremity point. In this figure the treatment target 320 and organ at risk 510 are shown. In this figure only part of the treatment target 320 is covered by the outline of the radiation beam 420. According to embodiments of the invention, only the volume of the treatment target that is within the actual outline of the radiation beam 520 will be considered for determining the 3D extremity point.

In most of the embodiments described above the position and/or orientation is determined by the direction and/or shape of the actual radiation beam. According to other embodiments the position and/or orientation of the view plane is determined information about the treatment target and/or organ at risk. For example, the view plane could be positioned such that the centre of mass of the treatment target is within the view plane. Also, for example the selection means could be configured to select the view plane such that a main motion vector of the treatment target and/or organ at risk is contained in the view plane. This main motion vector can for example be determined based on prior knowledge, e.g. the direction of breathing or bowel related motion may be known. Alternatively, the ultrasound guided radiotherapy system could be configured to store a time-history of treatment target positions (e.g. over the last 5 seconds or longer). From these positions a main motion vector could be extracted.

Figure 6:
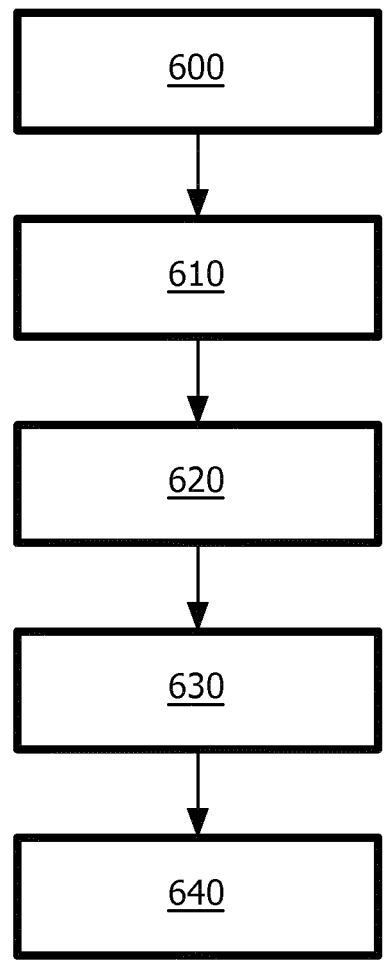

FIG. 6 diagrammatically shows a method for assisting in validating if an intrafraction motion of a treatment target and/or organ at risk remains within a preset limit during radiotherapy, wherein the method comprises the following steps:

controlling a radiotherapy system to provide a radiation treatment by means of radiation beams to a treatment target, wherein the radiation beams are provided to the treatment target from different directions 600 and acquiring a 3D online image of the treatment target during the radiation treatment by means of ultrasound 610 and detecting the treatment target and/or organ at risk on the 3D online image 620;

selecting a view plane through the detected treatment target and/or organ at risk 630 and;

displaying a 2D slice comprising an image of part of the treatment target and/or organ at risk along the view plane and displaying a treatment margin and/or an outline of the actual radiation beam in relation to the treatment target and/or organ at risk 640.

Whilst the invention has been illustrated and described in detail in the drawings and foregoing description, such illustrations and description are to be considered illustrative or exemplary and not restrictive; the invention is not limited to the disclosed embodiments and can be used for intra-fraction motion surveillance in the field of image guided radiotherapy.

The invention claimed is:

1. An ultrasound guided radiotherapy system, comprising
a radiotherapy system configured for providing a radiation treatment by means of a radiation beam to a treatment target and
an ultrasound imaging system configured for acquiring a 3D online image of the treatment target and/or an organ at risk during the radiation treatment and
detection means configured for detection, in the 3D online image, parts representing the treatment target and/or organ at risk;
selection means configured for selecting a view plane through the treatment target and/or an organ at risk represented by the detected parts in the 3D online image;
a display configured to display a 2D image of part of the treatment target and/or organ at risk along the view plane, wherein the display is further configured to display a treatment margin and/or an outline of an actual radiation beam in relation to the treatment target and/or organ at risk.

2. An ultrasound guided radiotherapy system as claimed in claim 1, wherein the selection means is configured to select the view plane based on an actual direction of the actual radiation beam.

3. An ultrasound guided radiotherapy system as claimed in claim 2, wherein the selection means is configured to select the view plane such that the actual direction of the actual radiation beam is substantially perpendicular to the view plane.

4. An ultrasound guided radiotherapy system as claimed claim 2, wherein the selection means is configured to select the view plane such that in the 2D slice along the view plane an outline of the treatment margin best matches according to a predetermined criterion a cross-sectional outline of the radiation beam.

5. An ultrasound guided radiotherapy system as claimed in claim 1, wherein the selection means is configured to select the view plane based on information about the treatment target and/or the organ at risk.

6. An ultrasound guided radiotherapy system as claimed in claim 5, wherein the selection means is configured to select the view plane such that a main motion vector, indicating a motion most relevant for quality assurance of the radiation treatment is contained in the view plane.

7. An ultrasound guided radiotherapy system as claimed in claim 5, wherein the selection means is configured to select the view plane such that the centre of mass of the treatment target is within the 2D slice along the view plane.

8. An ultrasound guided radiotherapy system as claimed in claim 2, wherein the selection means is configured to select the view plane such that the 2D slice along the view plane comprises a 3D extremity point of the treatment target, wherein the extremity point is the point of the treatment target that if inside a volume enclosed by the treatment margin or the actual outline of the radiation beam is closest to the treatment margin or the actual outline of the radiation beam or if exceeding the volume enclosed by the treatment margin or the actual outline of the radiation beam is furthest from the treatment margin or the actual outline of the radiation beam.

9. An ultrasound guided radiotherapy system as claimed in claim 8, wherein the only a part of the treatment target that is within the actual radiation beam is considered to determine the 3D extremity point.

10. An ultrasound guided radiotherapy system as claimed in claim 2, wherein the radiotherapy system comprises multiple collimator leaves and wherein the display is configured to display subsequent images and wherein the display is further configured to display a projection of the multiple collimator leaves and to display the subsequent images such that the orientation of the multiple collimator leaves is the same in the subsequent images.

11. An ultrasound guided radiotherapy system as claimed in claim 1, wherein the detection means is configured to register the online image to a treatment planning image.

12. An image guided radiotherapy system as claimed in claim 1, wherein the display is further configured to visualize the position of the view plane relative to the 3D online image or an illustration of a subject's anatomy.

13. Selection means configured for use in an ultrasound guided radiotherapy system according to claim 2.

14. A method for assisting in validating if an intrafraction motion of a treatment target and/or organ at risk remains within a preset limit during radiotherapy, wherein the method comprises the following steps:

controlling a radiotherapy system to provide a radiation treatment by means of radiation beam to a treatment target, wherein the radiation beam is provided to the treatment target from different directions and
acquiring a 3D online image of the treatment target during the radiation treatment by means of ultrasound and
detecting parts of the 3D online image representing the treatment target and/or organ at risk and;
selecting a view plane through the detected treatment target and/or organ at risk and;
displaying a 2D slice comprising an image of part of the treatment target and/or organ at risk along the view plane and displaying a treatment margin and/or an outline of the actual radiation beam in relation to the treatment target and/or organ at risk.

15. Computer program product comprising program code means for causing a computer to control an apparatus as claimed in claim 1 and to carry out the steps of the method when the computer program is carried out on the computer.

\* \* \* \* \*